(12) United States Patent
Wade

(10) Patent No.: US 12,383,116 B2
(45) Date of Patent: *Aug. 12, 2025

(54) SYSTEM AND METHOD FOR ENHANCED DATA ANALYSIS WITH VIDEO ENABLED SOFTWARE TOOLS FOR MEDICAL ENVIRONMENTS

(71) Applicant: Jack Wade, La Jolla, CA (US)

(72) Inventor: Jack Wade, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/235,352

(22) Filed: Aug. 18, 2023

(65) Prior Publication Data

US 2024/0122448 A1   Apr. 18, 2024

Related U.S. Application Data

(63) Continuation of application No. 17/338,599, filed on Jun. 3, 2021, now Pat. No. 11,744,441, which is a
(Continued)

(51) Int. Cl.
*A61B 1/00* (2006.01)
*A61B 1/04* (2006.01)
(Continued)

(52) U.S. Cl.
CPC ...... *A61B 1/0005* (2013.01); *A61B 1/000095* (2022.02); *A61B 1/043* (2013.01);
(Continued)

(58) Field of Classification Search
None
See application file for complete search history.

(56) References Cited

U.S. PATENT DOCUMENTS 6,271,752 B1 *  8/2001  Vaios .................... H04N 7/141
                                                    348/E7.086
6,285,902 B1 *  9/2001  Kienzle, III ....... A61B 17/1721
                                                    378/205

(Continued)

*Primary Examiner* — Nancy Bitar
(74) *Attorney, Agent, or Firm* — Olivo IP Law Group, P.C.; John W. Olivo, Jr.

(57) ABSTRACT

Medical software tools platform utilizes a surgical display to provide access to specific medical software tools, such as medically-oriented applications or tools, that can assist those in the operating room, such as a surgeon or surgical team, with a surgery. In particular, an optical sensor located within an endoscopic camera may register subtle differences in color characteristics reflected from a tissue surface and in turn transmit the information to a medical image processing system. Moreover, the new tools are intended to help surgeons better determine the boundaries between healthy and diseased regions during surgical procedures. Various tools are intended to be used in procedures where indocyanine green (ICG) fluorescent dye is used. Intraoperative fluorescence imaging is commonly used during minimally invasive procedures to enable surgeons to visualize tissue perfusion and anatomical structures. The term perfusion refers to the passage of blood and tissue fluid through the capillary bed. Intraoperative fluorescence imaging can also be used to improve visualization of vessels and structures, which, in turn, may reduce the risk of complications during minimally invasive surgeries.

20 Claims, 11 Drawing Sheets

Related U.S. Application Data continuation of application No. 16/677,584, filed on Nov. 7, 2019, now Pat. No. 11,051,891, which is a continuation of application No. 15/958,944, filed on Apr. 20, 2018, now Pat. No. 10,507,065, which is a continuation-in-part of application No. 15/789,948, filed on Oct. 20, 2017, now abandoned, which is a continuation-in-part of application No. 15/652,031, filed on Jul. 17, 2017, now Pat. No. 10,433,917, which is a continuation-in-part of application No. 15/456,458, filed on Mar. 10, 2017, now Pat. No. 10,758,314, which is a continuation-in-part of application No. 15/377,817, filed on Dec. 13, 2016, now abandoned, said application No. 16/677,584 is a continuation-in-part of application No. 15/170,575, filed on Jun. 1, 2016, now Pat. No. 10,142,641, said application No. 15/377,817 is a continuation of application No. 14/107,329, filed on Dec. 16, 2013, now Pat. No. 9,526,586, said application No. 15/170,575 is a continuation of application No. 13/430,489, filed on Mar. 26, 2012, now abandoned, which is a continuation-in-part of application No. 12/776,048, filed on May 7, 2010, now Pat. No. 8,266,333.

(60) Provisional application No. 61/865,037, filed on Aug. 12, 2013, provisional application No. 61/234,577, filed on Aug. 17, 2009, provisional application No. 61/182,624, filed on May 29, 2009.

(51) Int. Cl.
*A61B 1/313* (2006.01)
*A61B 34/00* (2016.01)
*A61B 90/00* (2016.01)
*G16H 10/60* (2018.01)
*G16H 20/17* (2018.01)
*G16H 20/40* (2018.01)
*G16H 30/40* (2018.01)
*G16H 40/63* (2018.01)
*G16H 50/70* (2018.01)

(52) U.S. Cl.
CPC ............ *A61B 34/25* (2016.02); *G16H 10/60* (2018.01); *G16H 20/17* (2018.01); *G16H 20/40* (2018.01); *G16H 30/40* (2018.01); *G16H 40/63* (2018.01); *G16H 50/70* (2018.01); *A61B 1/3132* (2013.01); *A61B 2034/256* (2016.02); *A61B 90/361* (2016.02); *G06T 2200/24* (2013.01); *G06T 2207/30004* (2013.01)

(56) References Cited

U.S. PATENT DOCUMENTS

| | | | | |
|---|---|---|---|---|
| 7,039,723 | B2* | 5/2006 | Hu | G16H 30/20 709/248 |
| 8,295,649 | B2* | 10/2012 | Berini | G06V 10/94 382/304 |
| 2003/0051021 | A1* | 3/2003 | Hirschfeld | H04L 67/1027 709/223 |
| 2003/0104806 | A1* | 6/2003 | Ruef | H04M 3/42 348/E7.079 |
| 2003/0159141 | A1* | 8/2003 | Zacharias | H04N 5/445 348/E5.093 |
| 2008/0071144 | A1* | 3/2008 | Fein | A61B 1/07 600/178 |
| 2012/0330103 | A1* | 12/2012 | Tenger | A61M 16/0429 600/188 |
| 2014/0171759 | A1* | 6/2014 | White | A61B 5/6835 600/306 |
| 2015/0282749 | A1* | 10/2015 | Zand | A61B 1/0676 600/301 |
| 2016/0166336 | A1* | 6/2016 | Razzaque | A61B 90/37 606/130 |
| 2019/0133711 | A1* | 5/2019 | Wade | G16H 30/40 |

* cited by examiner

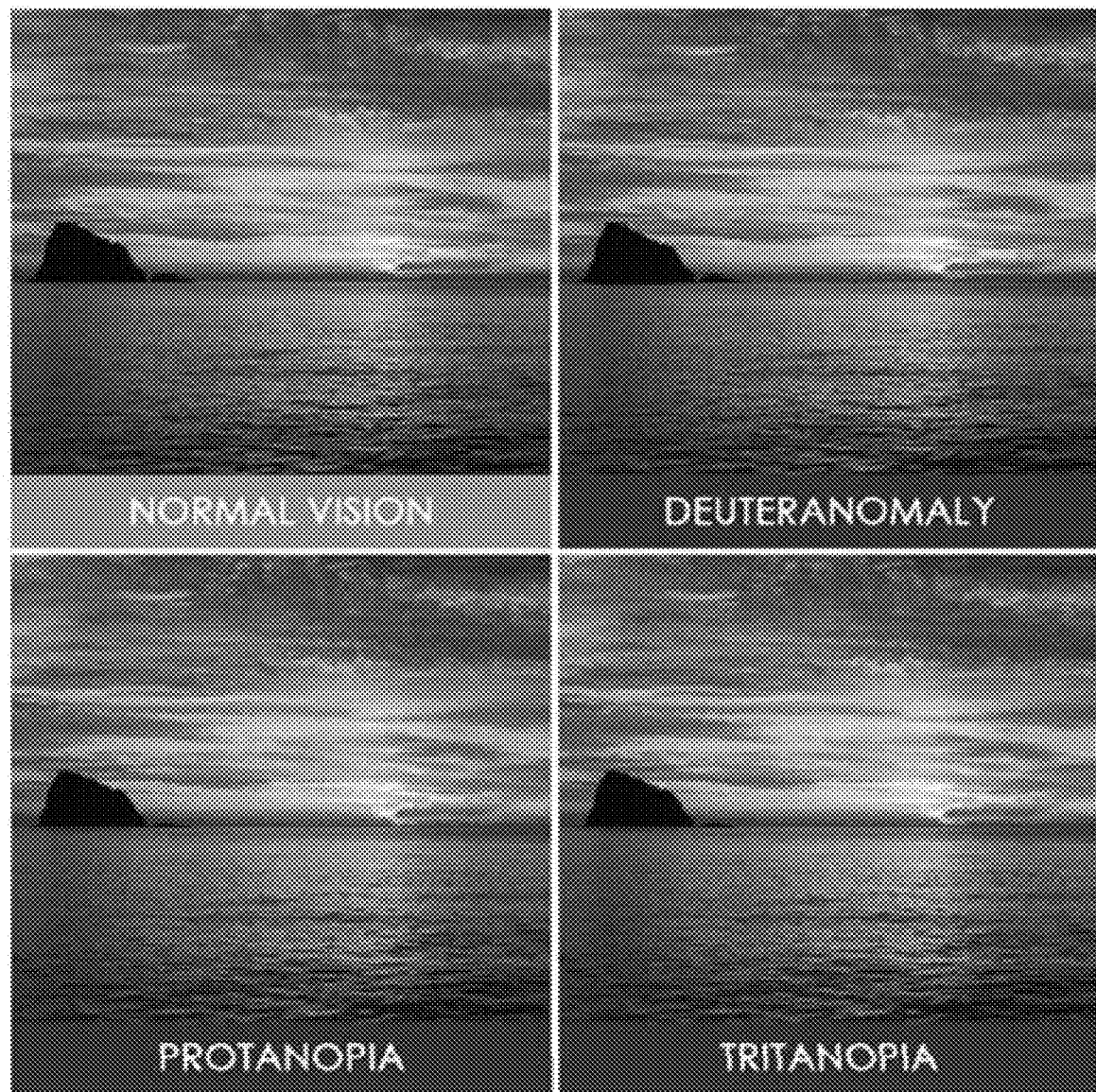
FIG. 9.1

SYSTEM AND METHOD FOR ENHANCED DATA ANALYSIS WITH VIDEO ENABLED SOFTWARE TOOLS FOR MEDICAL ENVIRONMENTS

PRIORITY CLAIM

This application is a continuation of U.S. patent application Ser. No. 17/338,599, filed Jun. 3, 2021, which is a continuation of U.S. patent application Ser. No. 16/677,584, filed Nov. 7, 2019, which is a continuation of U.S. patent application Ser. No. 15/958,944, filed Apr. 20, 2018, and issued as U.S. Pat. No. 10,507,065 on Dec. 17, 2019, which is a continuation in part of U.S. patent application Ser. No. 15/789,948, filed Oct. 20, 2017, which is a continuation in part of U.S. patent application Ser. No. 15/652,031, filed Jul. 17, 2017, issued as U.S. Pat. No. 10,433,917, on Oct. 8, 2019, which is a continuation in part of U.S. patent application Ser. No. 15/456,458, filed Mar. 10, 2017, which is a continuation in part of U.S. patent application Ser. No. 15/377,817, filed Dec. 13, 2016, which is a continuation of U.S. patent application Ser. No. 14/107,329, filed Dec. 16, 2013, and issued as U.S. Pat. No. 9,526,586 on Dec. 27, 2016, which claims the benefit of U.S. Provisional Patent Application Ser. No. 61/865,037, filed Aug. 12, 2013. This application also claims the benefit of and is a continuation in part of U.S. patent application Ser. No. 15/170,575, filed Jun. 1, 2016, issued as U.S. Pat. No. 10,142,641, on Nov. 27, 2018, which is a continuation of U.S. patent application Ser. No. 13/430,489, filed Mar. 26, 2012, which is a continuation-in-part of U.S. patent application Ser. No. 12/776,048, filed May 7, 2010, and issued as U.S. Pat. No. 8,266,333, on Sep. 11, 2012, which claims the benefit of U.S. Provisional Patent Applications Ser. No. 61/182,624, filed May 29, 2009, and 61/234,577, filed Aug. 17, 2009. Each of the foregoing applications is hereby incorporated by reference.

TECHNICAL FIELD

The technology disclosed herein relates to medical software tools and, in particular, some embodiments relate to systems and methods for a software tools platform in a medical environment, such as a surgical environment, incorporating enhanced data analysis.

BACKGROUND OF THE INVENTION

Disclosed herein is an updated medical software tool platform, aka surgeon's dashboard, comprised of a new set of desktop tools (aka widgets) developed to help medical professionals identify subtle changes in tissue. Various tools are intended to be used in procedures where indocyanine green (ICG) is used. ICG is a fluorescent dye and a marker in the assessment of the perfusion of tissues and organs. The term perfusion refers to the passage of blood and tissue fluid through the capillary bed. Moreover, the new tools are intended to help surgeons better determine the boundaries between healthy and diseased regions during surgical procedures. Intraoperative fluorescence imaging is commonly used during multiple minimally invasive procedures to enable surgeons to visualize tissue perfusion and anatomical structures. The fluorescent imaging agent binds to protein in blood and is metabolized and excreted by the liver thereby providing laparoscopic visualization of the hepatic artery and bile ducts. These dyes enable a precise visual assessment of blood flow in vessels, as well as the quality of tissue perfusion in, for example, colorectal, esophageal and bariatric surgeries. Intraoperative fluorescence imaging can also be used to improve visualization of vessels and structures, which, in turn, may reduce the risk of complications during minimally invasive surgeries.

Various desktop tools are designed to be used in conjunction with ICG to enhance a surgeon's ability to visualize and analyze tissue perfusion and structural anatomy intraoperatively and in real-time. In certain situations, the tools can be used to help the surgeon visualize and objectively analyze different levels of blood flow in tissue. Moreover, various desktop tools may assist surgeons in making critical decisions in the operating room, which can potentially reduce rates of postoperative complications and decrease healthcare costs.

The new medical software tools include 1) ICG Visualization, 2) Instant Replay, 3) Height Mapping, 4) Grid Tool, 5) Perfusion Visualization and Quantification, 6) Color Collaboration. Each of the individual tools are depicted in the figures below and described in the narrative that follows.

SUMMARY OF THE INVENTION

Various embodiments of the disclosed technology provide a medical software tools platform that utilizes a surgical display to provide access to medical software tools, such as medically-oriented applications or widgets, that can assist those in the operating room, such as a surgeon and their surgical team, with a surgery. For various embodiments, the medical software tools platform and its associated medical software tools are presented on a surgical display (e.g., being utilized in an operating room) over an image stream provided by a surgical camera (e.g., in use in the operating room) or other medical device that generates image streams. An image stream can include video or a series of static images (e.g., medical ultrasound device). Various medical software tools can provide features and functions that can facilitate integration of equipment in an operating room or add medical context awareness to anatomic structures presented in the image stream from the surgical camera.

Medical video display panels and multiscreen displays are commonly employed in such contexts as hospital operating theaters or any facility where surgical operations are carried out in a sterile environment. They are used to display visual information from data streams such as surgical imagery from an endoscope, patient vital signs, patient medical records, clinical imaging data (patient CT scans, MRIs, etc.), outputs from other operating room equipment, and operating room environmental status. Surgical displays and multiscreen video displays provide a surgeon and their surgical team with visual information that can be automatically updated, or can be used to enable collaboration among viewers. Where a surgical display or multiscreen video display is used for group collaboration, there is generally a requirement that the group has the ability to update and reconfigure the visual information displayed, which is usually facilitated through a video switch. Traditional video switches are controlled through a switch box, a keyboard, or a local connection (via an RS-232 port or Ethernet port) and have only a single point for control access. In some contexts, visual data streams to a single large panel video display or a multiscreen display configuration are provided by two or more computer systems, each being controlled by a computer operator (i.e., user) using such input/output (IO) devices as keyboards, mice, and as video monitor.

One of ordinary skill in the art would understand that, depending on the embodiment, either the image stream input interface, the image stream output interface, or both may utilize unidirectional communication or bidirectional communication with input devices and output devices. For example, a system may be configured to receive control information from a controller interface device via an image stream output interface, or to send control information to an image source via an image stream input interface. In another example, the control information is received by the system through the Display Data Channel (DDC). Depending on the embodiment, the system may be configured to send control information to a device external to the system, through the image stream input interface.

In some embodiments, the switching matrix may selectively map an image stream input interface or a processed image stream in real-time. In further embodiments, the switching matrix may selectively map the image stream input interface to more than one image processing module or to more than one image stream output interface simultaneously. Additionally, in some embodiments, the switching matrix may selectively map the processed image stream to more than one image processing module or to more than one image stream output interface simultaneously. In other embodiments, the switching matrix may selectively map an image stream input interface or the processed image stream based on a criterion. For example, the switching matrix may selectively map an image stream input interface or a processed image stream based on its source or content. In another example, the switching matrix may selectively map a processed image stream based on the results of a preceding image processing module. Depending on the embodiment, the image processing module may have the capability of processing a plurality of image streams in parallel. The image stream interface for some embodiments may be configured to receive the image stream from an image stream capture device, an image stream playback device, a computer system, a sensor device or a medical device (e.g., endoscope). The image stream output interface for some embodiments may be configured to output to a display (e.g., liquid crystal display monitor), a computer system, or recording device (e.g., digital video recorder). Further, in some embodiments, the system may be configured to output an image stream through a virtual display.

In numerous embodiments, the system further comprises a data input interface, wherein the switching matrix is further in communication with the data input interface such that the switching matrix can further selectively map the data input interface to the image stream output interface or to the first image processing module. For some such embodiments, the image stream input interface may comprise the data input interface.

For some embodiments, dynamic selection with respect to inputs means that one or more inputs can be selected or unselected in real time for routing to one or more image processing elements. For additional embodiments, dynamic and iterative selection with respect to processing elements means that a selected image stream can be routed to one or more image processing elements simultaneously and in real time. The routing may be based upon criteria relating to the image stream's source, the image stream's content, or on the processing results of a preceding image processing element. The output of an image processing element may be directed back to the system or method for routing to a subsequent image processing element, or to one or more image outputs that supply an image stream to an output device (e.g., display, image recorder, or other image processor, or transmission device).

An exemplary system for switching control between a plurality of computer systems, comprising a plurality of image stream input interfaces, wherein a first image stream input interface of the plurality of image stream input interfaces is configured to couple with a first computer system of the plurality of computer systems, and wherein a second image stream input interface of the plurality of image stream input interfaces is configured to couple with a second computer system of the plurality of computer systems. The system may further comprise a plurality of computer input device interfaces (e.g., Universal Serial Bus [USB], PS/2, AT connector, Bluetooth, Infrared [IF], or FireWire), wherein a first computer input device interface of the general plurality of computer input device interfaces is configured to couple with the first computer system, and wherein a second computer input device interface of the plurality of general computer input device interfaces is configured to couple with the second computer system.

The system may additionally comprise: an ICG visualization tool that enables the visualization of perfusion of the ICG agent to help identify healthy tissue; an Instant Replay tool that enables a surgeon to replay a portion of the surgical video and to slow down the visual presentation of the absorption process to better characterize the differences in neighboring tissue; a Height Mapping tool that allows mapping of green intensity to reveal greater detail in the presence of ICG; a Grid Tool that overlays a dynamically adjustable grid over a selected area of the surgical video. The number of grid lines along the x and y axes can be increased or decreased by user on the fly; a Perfusion Visualization and Quantification tool that brings up a panel that quantifies the degree and rate of selected tissue to absorb and dissipate contrast fluid (ICG) injected into a patient's blood stream; and a Color Collaboration tool that allows the surgeon to personalize gamma adjustments in real time. The colors are adjusted and displayed to a standard unique to each individual user.

Other embodiments provide for a computer readable storage medium having instructions embedded thereon to cause a processor to perform operations similar to those described above with respect to the various systems and methods in accordance with the present invention. Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

FIG. 9.1 is an example of different types of color processing for the Color Collaboration tool.

DETAILED DESCRIPTION OF THE
PREFERRED EMBODIMENT

Figure 1:
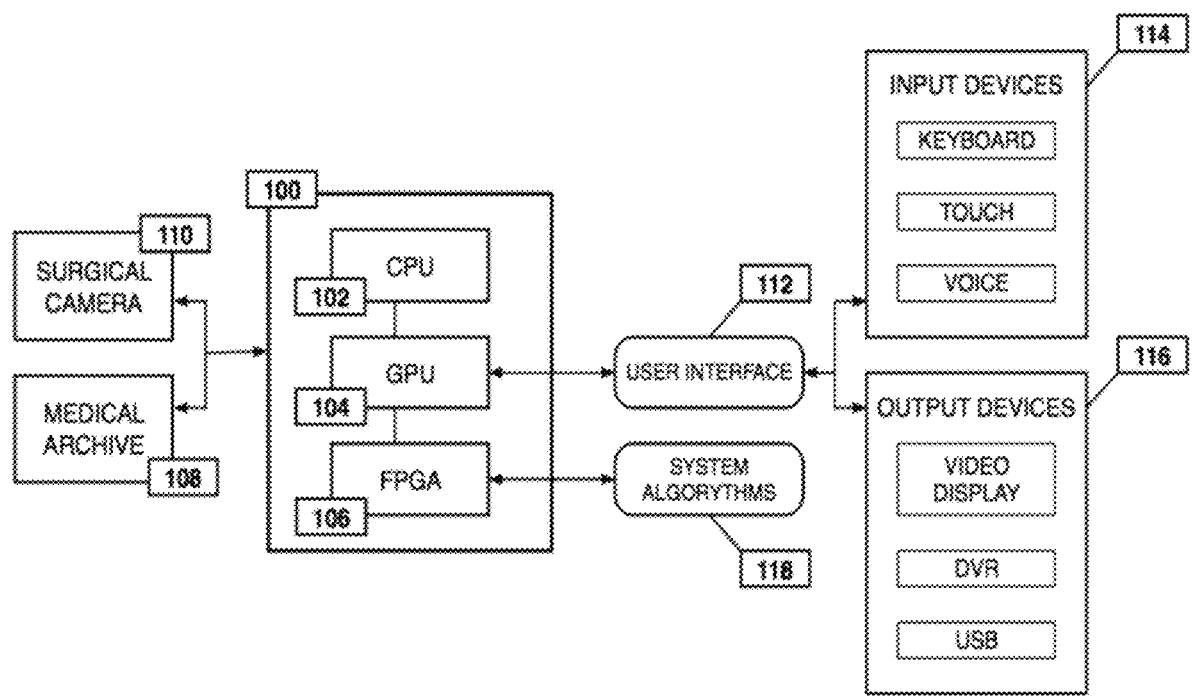
FIG. 1 is a block diagram illustrating an example of the overall processing system that may be used in implementing various features of embodiments of the disclosed technology.

FIG. 1 is a block diagram illustrating an example of the overall processing system that may be used in implementing various features of embodiments of the disclosed technology. In accordance with the preferred embodiment of the present invention, the processing system 100 consists of processor elements such as: a central processing unit (CPU) 102; a graphics processing unit (GPU) 104; and a field programmable gate array (FPGA) 106. The processing system 100 may be used to retrieve and process raw data derived from a surgical camera 110 or a data storage device, such as a medical archive 108. The surgical camera 110 or medical archive 108 transmits a data stream to the processing system 100, whereby that data is processed by the CPU 102. The FPGA 106, connected to the CPU 102 and the GPU 104, simultaneously processes the received data by using a series of programmed system algorithms 118, thus functioning as an image clarifier within the processing system 100. The GPU 104 communicates with the user interface 112 to display the received data from the medical archive 108. The GPU 104 enables the user interface to then communicate the data to connected input devices 114 and output devices 116. The user interface 112 can communicate to multiple input 114 and output devices 116 simultaneously. An input device 114 can include, for example, a keyboard, touchscreen or voice activated device. An output device 116 can include, for example, a video display, a digital video recorder (DVR) or universal serial bus (USB).

Figure 2:
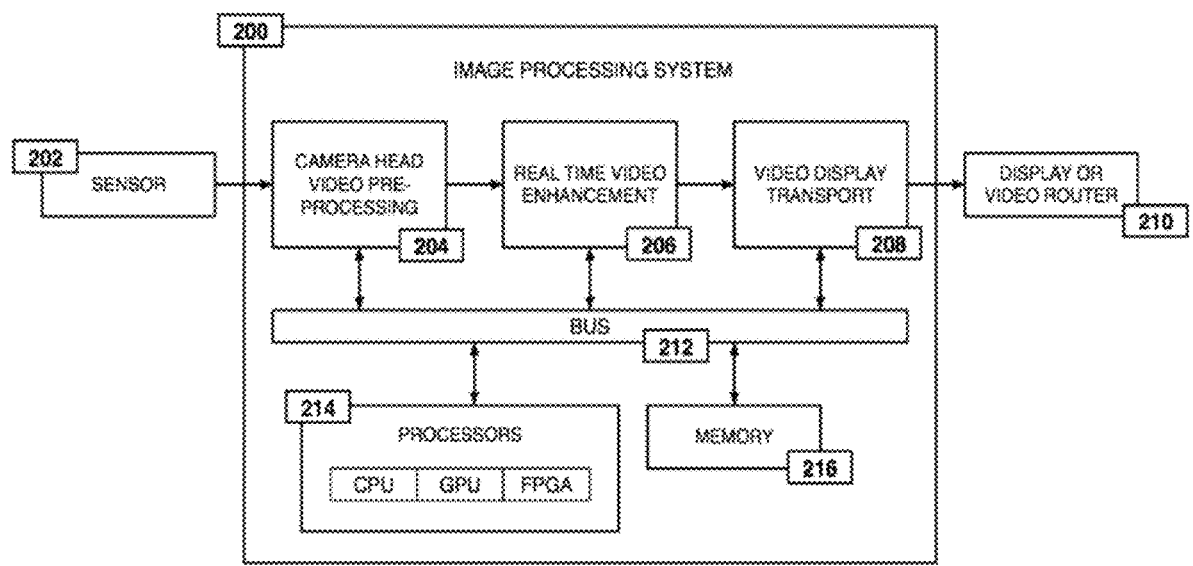
FIG. 2 is a block diagram illustrating an example of the image processing system that may be used in implementing various features of embodiments of the disclosed technology.

FIG. 2 is a block diagram illustrating an example of the image processing system that may be used in implementing various features of embodiments of the disclosed technology. In accordance with the preferred embodiment of the present invention, the image processing system 200 consists of three components that process image data received from a sensor 202 in order to send that data to a display or video router 210. The three components of the image processing system 200 are: camera head video pre-processing 204; real time video enhancement 206; and the video display transport 208 function. Image data is collected by a sensor imaging device 202, and is then transmitted to the camera head video pre-processing component 204 within the image processing system 200. This data may be, for example, a raw video image that is pre-processed using various image processing algorithms. Image pre-processing may also include software modules for image registration and segmentation to optimize the video data and communicate via the system bus 212 with the internal system processors 214: the CPU; GPU; and FPGA.

The pre-processed image data is transmitted to the real time video enhancement 206 component, whereby the image data is enhanced to improve clarity or highlight certain details. Once the image data resolution has been enhanced, the video display transport 208 component completes image post-processing, formatting from the initial sensor resolution to the eventual display resolution, for example, enhancing the video data to 1080p HD or 4K display resolution or using software modules such as video cross conversion, scaling and adding graphic overlays. The processed image data is then transmitted from the image processing system 200 to the display or video router 210. The video display transport also saves the processed image data to the processing system memory 216 that can consist of internal and external memory storage.

Figure 3:
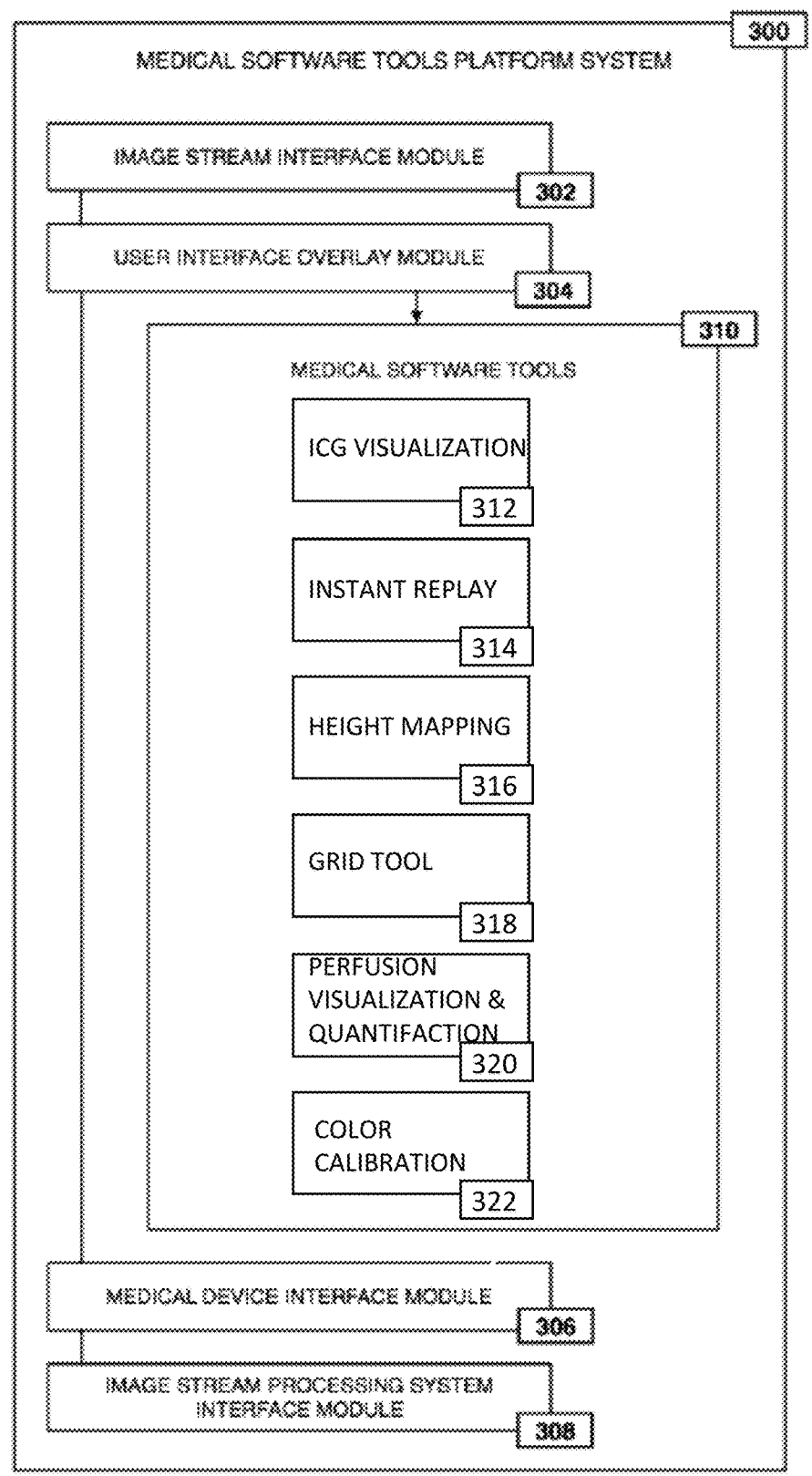
FIG. 3 is a block diagram illustrating an example medical software tools platform in accordance with some embodiments of the technology described herein.

FIG. 3 is a block diagram illustrating an example medical software tools platform system in accordance with some embodiments of the technology described herein. The medical software tools platform provides access to medically-oriented applications (apps) or tools that can assist members of the surgical team during an operation. For example, many surgeries utilize ICG to enable surgeons to visualize tissue perfusion and anatomical structures, however, the camera sensor captures much more color detail that the human eye can discern. Therefore, the use of an ICG visualization tool can provide a more accurate and objective measure of the rate of perfusion. An instant replay tool enables the users to replay a portion of the surgical video in slow motion in order to more closely observe the process of perfusion. A height mapping tool provides a simulated 3D visualization that enables the user to quickly and accurately identify areas of highest absorption of the ICG fluorescent dye. A grid tool brings up an overlay that draws grid lines to provide an x,y location reference. This enables a surgeon to precisely mark the location of an anomaly or area of interest for future reference. A perfusion visualization and quantification tool precisely measure the rates of rise and decay of the of fluoresced pixel intensity. This is intended to assist a surgeon in identifying the borders between healthy and diseased tissue. A color calibration tool allows users to configure a color preference so that colors are adjusted and displayed to a standard unique to each individual. This enables color blind surgeons to better visualize information on the surgical display and perceive subtle changes in color.

In accordance with the preferred embodiment of the present invention, the medical software tools platform system 300 includes: an image stream interface module 302; a user interface overlay module 304; medical software tools 310; a medical device interface module 306; and an image stream processing system interface module 308. The medical software tools platform system 300 may be integrated, in whole or in part, into a video display or an image stream processing system utilized in an operating room. The image stream interface module 302 may receive an image stream acquired by a surgical camera or the like. Depending on the embodiment, the image stream may be received directly from the surgical camera, or may be provided by way of one or more components, such as an image stream processing system. The image stream received from the image stream interface module 302 may vary in resolution, frame rate, format, and protocol according to the surgical camera or the image stream processing system providing the image stream.

The user interface overlay module 304 may provide a user interface to the medical software tools platform system 300, which may include one or more graphical user interface (GUI) elements presented over the image stream received through the image stream interface module 302. For some embodiments, the user interface comprises a bottom toolbar configured to be presented over the image stream, and configured to provide access to various medical software tools 310 available through the medical software tools platform system 300.

The medical software tools platform system 300 may include one or more medical software tools, such as medically-oriented applications or widgets, which can be utilized with respect to the image stream being received through the image stream interface module 302. The medical software tools 310 include but are not limited to: a ICG Visualization module 312; an instant replay module 314; a height mapping module 316; a grid tool module 318; an perfusion visualization and quantification module 320; a color calibration module 322.

The medical device interface module 306 may facilitate communication between the medical software tools platform system 300, one or more of the medical software tools 310, and one or more various medical devices utilized in an operating room. The image stream processing system interface module 308 may facilitate communication between the medical software tools platform system 300 and an image stream processing system utilized to process an image stream acquired by a surgical camera or the like. Through the communication, the image stream processing system interface module 308 may transmit control data to an image stream processing system, or receive an image stream from a surgical camera as processed by the image stream processing system. The image stream processing system interface module 308 may include various data interfaces, including wired or wireless network interfaces and serial communication interfaces.

ICG Visualization (FIG. 4) tool enables the visualization of perfusion of the ICG agent to help identify healthy tissue. The ICG Visualization tool can be used in conjunction with other tools to enable the following capabilities: 1. Slow Motion—replaying the video in slow motion 2. Intensity—quantifying the degree of ICG absorption for defined areas of interest 3. Speed—measuring the time to full absorption for defined areas of interest 4. ICG Map—simulated 3D views of ICG absorption using intensity or speed of ICG data.

In a preferred embodiment the ICG Visualization tool can be used in conjunction with the Slow Motion Replay tool 402 and the Height Mapping tool 404, which can be integrated into the ICG Visualization user interface. In this implementation, a surgeon might use the ICG Visualization in conjunction with the Slow Motion Replay tool and the Height Mapping tools in a four step process as follows.

In a first step, a user, such as the surgeon or an assistant, uses the mouse to sweep an area of interest. The selected image segment is scaled and centered in the yellow working box as show in the upper left corner 408.

As ICG is administered, the computer measures time to reach full luminance. The example in FIG. 4 shows this time to be 12 seconds 410.

Video frames are cached in memory a full frame rate. Slow Motion replays are available at selected speeds and use motion-compensated frame interpolation for a smooth playback. An elevator bar on the right side is used to control image zoom.

Figure 4:
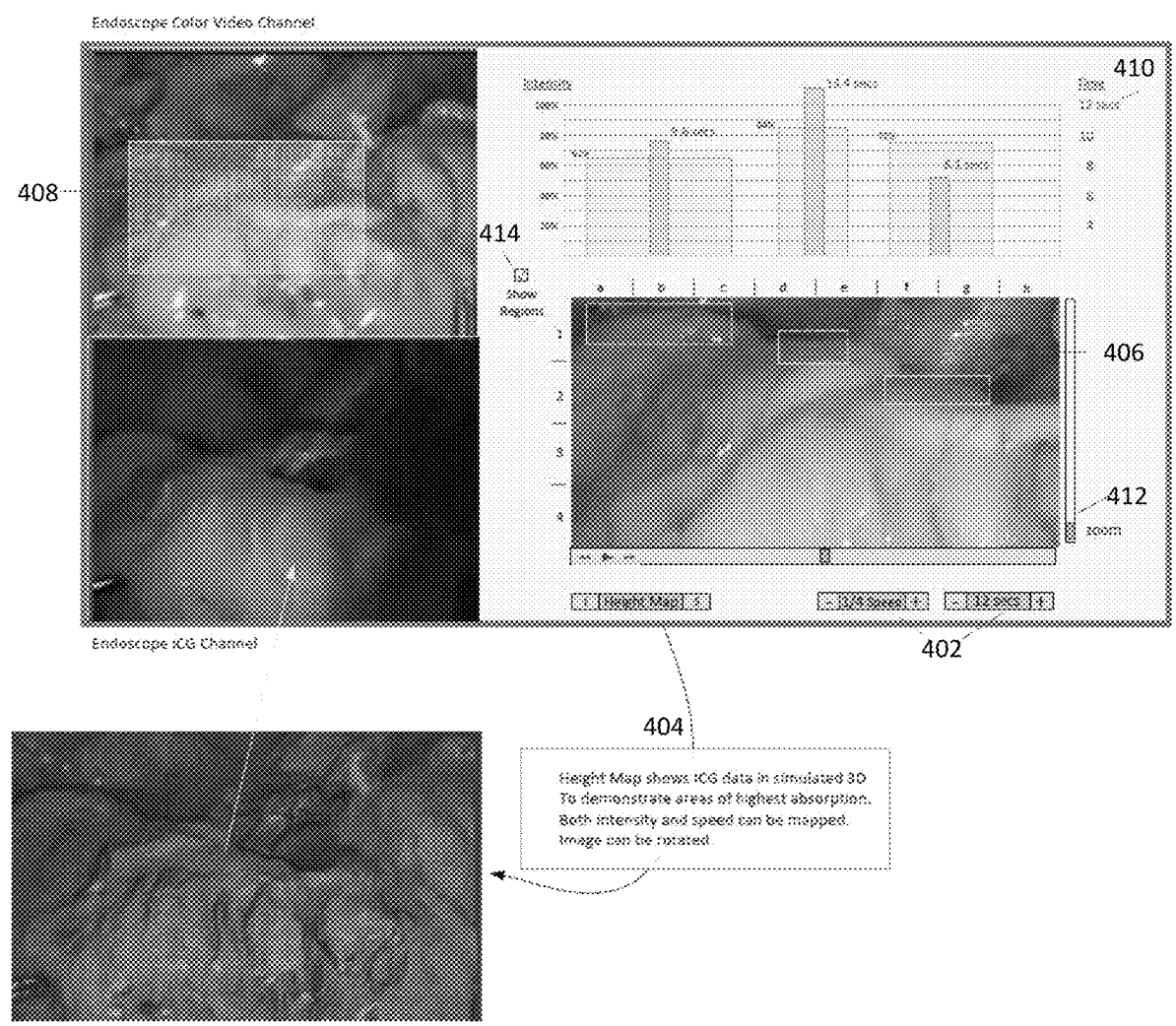
FIG. 4. ICG Visualization, a tool that enables the visualization of perfusion of the ICG agent to help identify healthy tissue.

In a second step, an operator uses the mouse to create a box around one or more regions of interest, as shown in FIG. 4 on the right where three yellow boxes are selected 406.

The intensity and the time to reach full intensity for each region is graphed using the ICG channel to provide a quantitative comparison 410.

Selected regions are described by outline boxes (dashed yellow areas in the example 406). Unchecking the form box labeled, "Show Regions" hides the outlines 414. Region outlines can be moved and resized with the graphs updated in real time.

In a third step, the system quantifies perfusion based on intensity (absorption) and speed 404.

In a fourth step, the user has the option to invoke slow motion instant replays at selectable speed so that the details of the process of perfusion can be reviewed and studied 402.

The user also has the option to invoke Height Map tool which shows ICG data in simulated 3D to demonstrate areas of highest perfusion. Both intensity and speed can be mapped and the image can be rotated 404.

Figure 5:
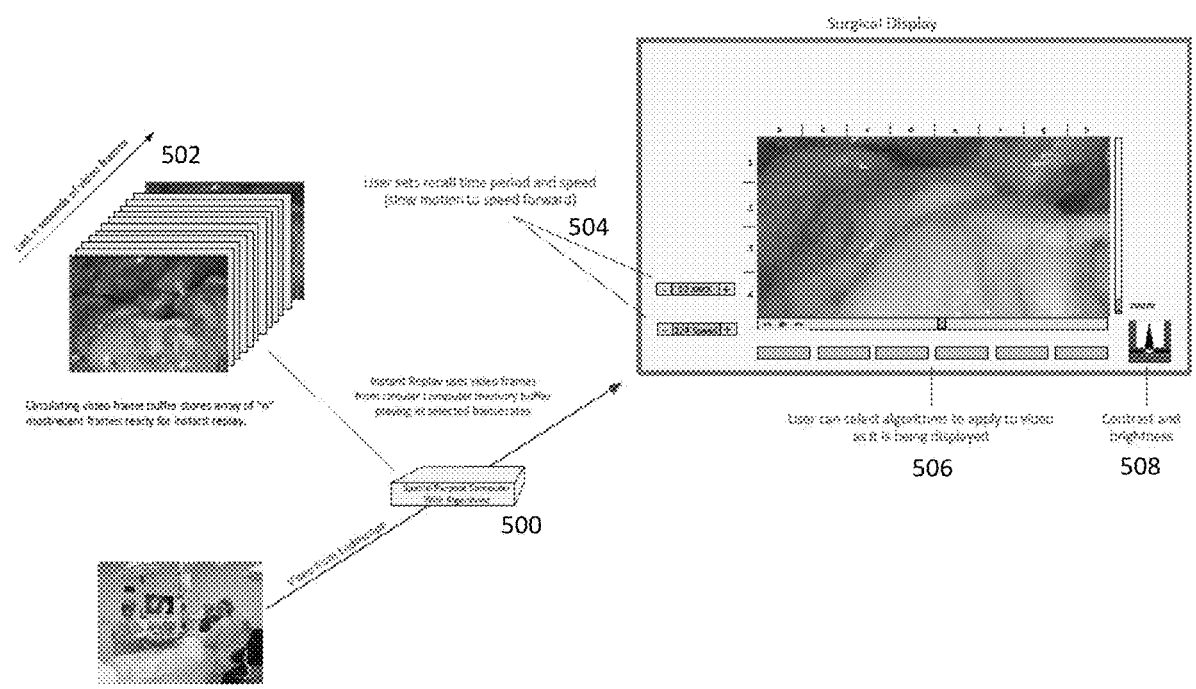
FIG. 5. Instant Replay, a tool that enables a surgeon to replay a portion of the surgical video and to slow down the visual presentation of the absorption process to better characterize the differences in neighboring tissue.

Instant Replay (FIG. 5) tool enables a surgeon to replay a portion of the surgical video. An example above described how Instant Replay can be used to review the speed of ICG contrast agent perfusion to provide the surgeon an opportunity to slow down the visual presentation of the absorption process to better characterize the differences in neighboring tissue. FIG. 5 shows how Instant Replay works. Video from the endoscope is recorded and stored in a special purpose computer that implements various image processing algorithms 500. The last n seconds of video frames are stored on a circular video frame buffer within the computer 502. Instant Replay uses video frames from the computer circular memory buffer, playing frames at selected frame rates. The user sets the recall time period and speed from slow motion to speed forward 504. The user can select algorithms to apply to the video as it is being displayed 506. The user can also select levels of contrast and brightness for the replay 508.

Figure 6:
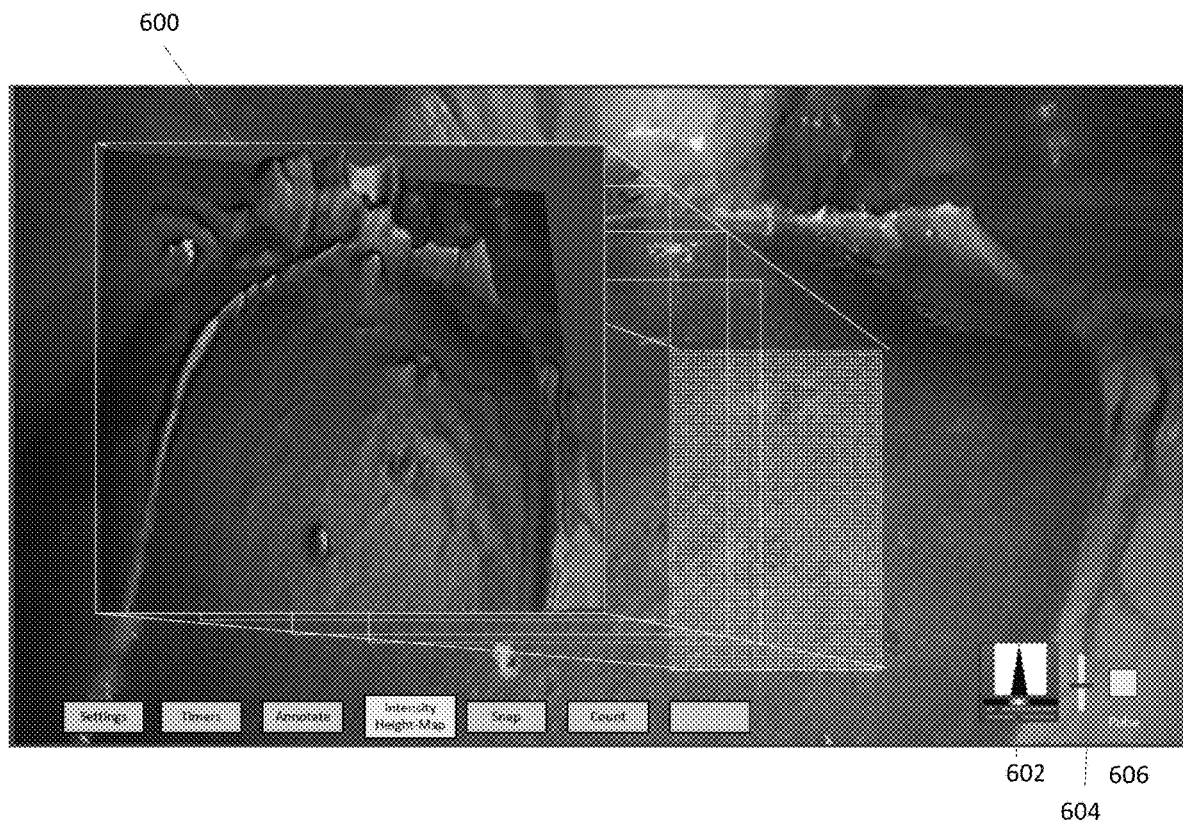
FIG. 6. Height Mapping, a tool that allows mapping of green intensity to reveal greater detail in the presence of ICG.

The Height Map tool is shown in FIG. 6. To use the tool, the user first sweeps an area of interest with the mouse. The selected area is enlarged and rendered as a "Picture-In-Picture" insert 600. The insert simulates a 3D view by mapping the area's pixels onto an elevation grid using the pixel intensities to create a height map. The user can experiment with different views and degrees of detail by rotating the insert in 3D using a mouse, adjusting for more or less detail with the window/level sliders 602, and by scaling with the vertical bar 604. The Pulse button 606 animates the pixel heights in relation to the intensity change resulting from the pulse of pumping blood into the local vascular network. This creates a visual effect of pixels dancing in synchronization with the patient's heartbeat. The rise and fall height and rate of change in pixel intensity demonstrate the different responses of diseased and healthy tissue.

Figure 7:
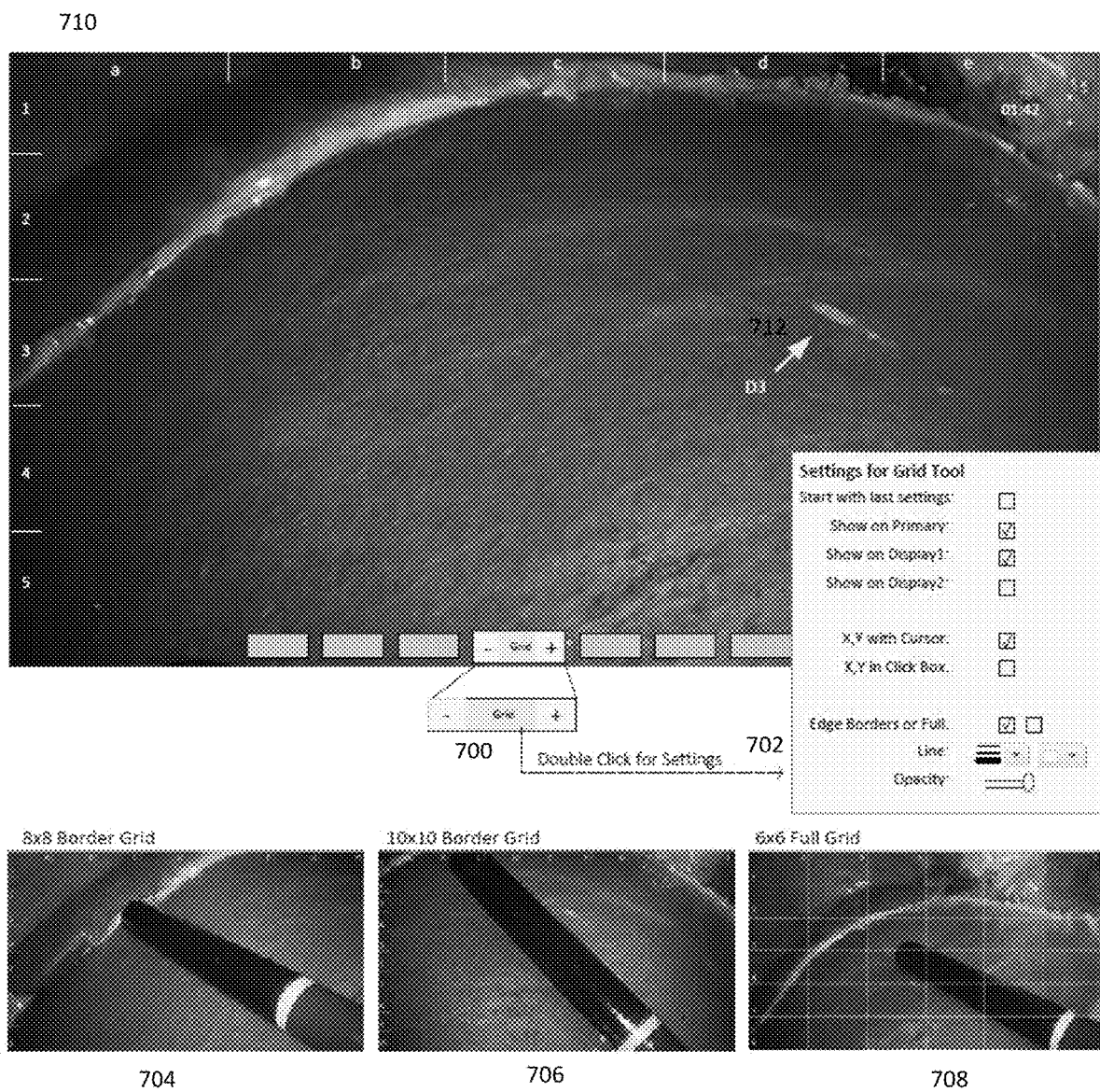
FIG. 7. Grid Tool, a tool that overlays a dynamically adjustable grid over a selected area of the surgical video. The number of grid lines along the x and y axes can be increased or decreased by user on the fly.

The Grid Tool is shown in FIG. 7. Selecting the Grid tool brings up an overlay that draws grid lines to provide an x,y location reference 710. The icon includes a "minus" and a "plus" touch point to grow or shrink the grid resolution 700. Double clicking brings up a sub-menu 702 to select full or border grid lines and select line color and opacity. Default settings from the Personal Preferences are used when the tool is initialized.

The grid is dynamically adjustable and the number of grid lines in x and y can be increased or decreased by user on the fly. The Grid Lines are selectable such that the user can select lines at borders 704, across full image 708, or none. Users can configure the attributes of the grid lines to set line weight, color and opacity 702. In multi-display environments, the user can select which displays have grid lines. The user can configure the systems to display the coordinates of the visible cursor location 712. This visual confirmation of cursor location can eliminate doubt and ease cognitive burden for the user. The system also offers the ability to save the personal settings for each user, including an option to recall "Last Used" settings.

Figure 8:
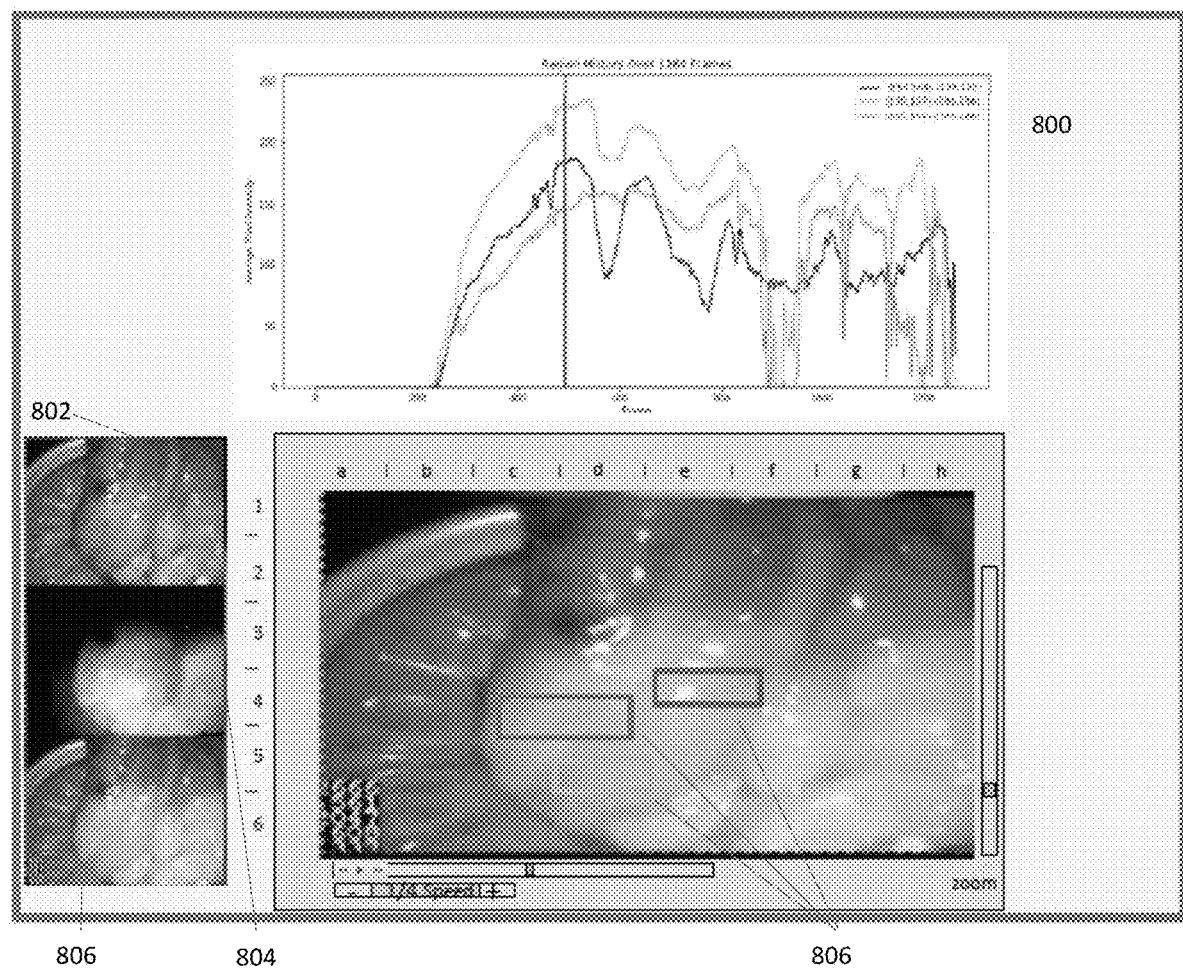
FIG. 8. Perfusion Visualization and Quantification, a tool that brings up a panel that quantifies the degree and rate of selected tissue to absorb and dissipate contrast fluid (ICG) injected into a patient's blood stream.

The Perfusion Visualization and Quantification tool is shown in FIG. 8. Selecting the Perfusion Visualization and Quantification tool brings up a panel that quantifies the degree and rate of selected tissue to absorb and dissipate contrast fluid (ICG) injected into a patient's blood stream 800. The tool displays both endoscopic video channels (RGB 802 and IR 804) and a third fused image with the IR illuminated tissue transformed to fluorescent green for overlay on the RGB image 806. The purpose is to assist the surgeon in characterizing the state of the tissue. Default settings from the Personal Preferences are used when the tool is initialized.

The user sweeps an area of interest 806 to see a graph of the average pixel intensity (Y-axis) plotted against time (X-axis) 800. The curve provides a quantitative measure of the tissue's absorption and decay rate for comparison with other areas to locate the healthiest tissue. Graphs respond in real time and may be moved about the image to explore responses. Graph results are plotted in different colors for comparison purposes 800.

The graph 800 provides an objective method to quantify the perfusion process using the degree of absorption and also the time to reach maximum intensity and the time to dissipate the agent. Without this tool, surgeons must rely on subjective measurements of color intensity and time.

The tool enables a user to measuring rise time, the time it takes for a fluoresced pixel intensity to achieve maximum luminance, and the decay time, the time it take for a fluoresced pixel intensity to achieve initial state. The instant replay feature allows the user to view the fluorescing period at selective speeds to better observe the process. A graphical representation shows the amplitude and time of the fluorescing event in real time 800. The tool is able to capture and compare multiple samples using software mechanisms to collect and compare multiple samples 806, 800.

Figure 9:
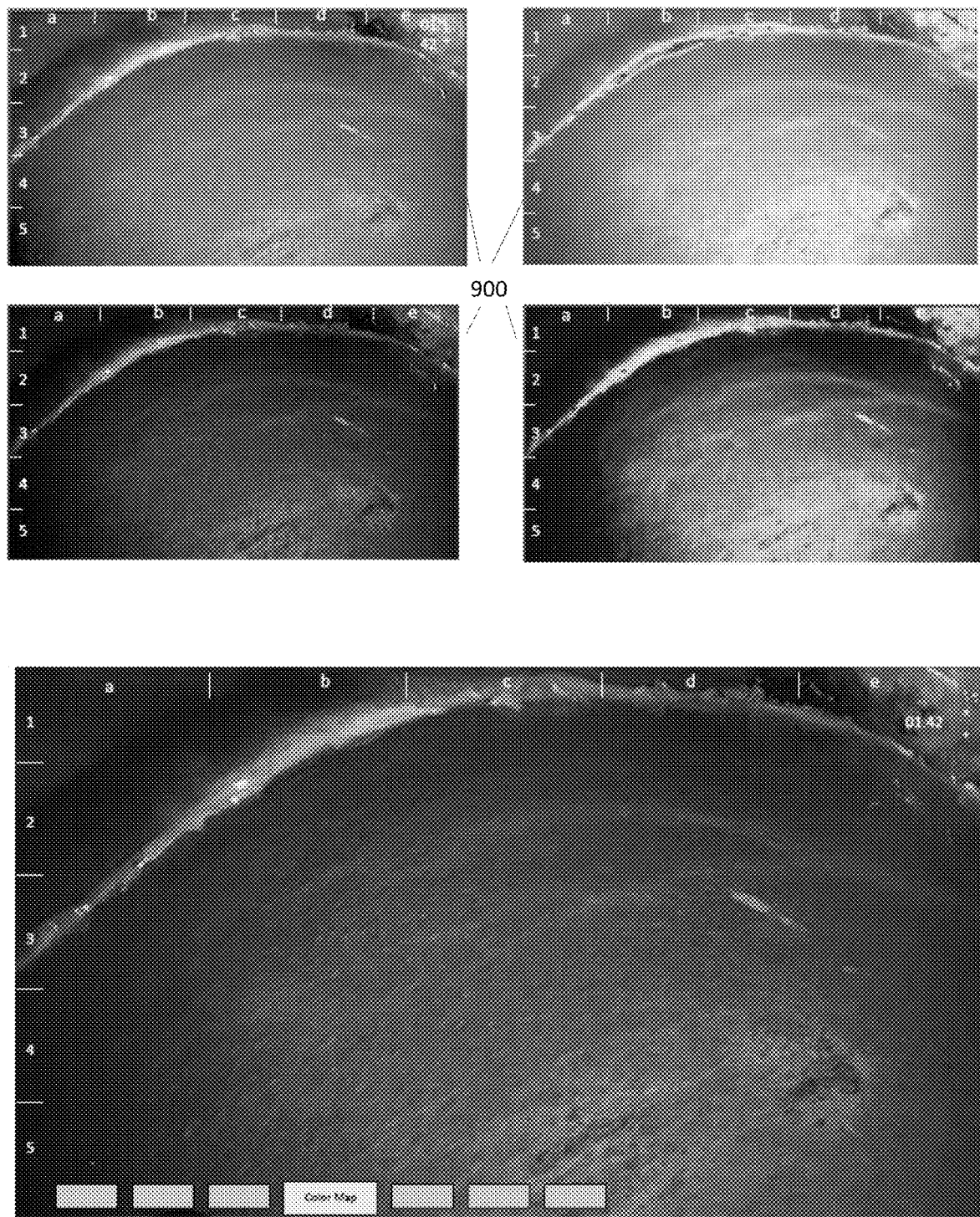
FIG. 9. Color Collaboration, a tool that allow the surgeon to personalized gamma adjustments in real time. The colors are adjusted and displayed to a standard unique to each individual user.

The Color Collaboration tool, shown in FIG. 9, presents the surgeon with a choice of views of the tissue surface with a choice of color maps 900. The goal is to more clearly characterize the margins of diseased tissue, based on the individual color preference of a user.

FIG. 9.1 is an example of different types of color processing for the Color Collaboration tool. In accordance with the preferred embodiment of the present invention, surgeons use color to identify and characterize tissue in many ways. However individual humans perceive color differently and surgery frequently involves a team of specialists, each perceiving color in their own way. Some form of color blindness effects ~8% of men and 0.5% of women and there are many types of color blindness—FIG. 9.1 illustrates three common forms of color blindness.

By first sampling a surgeon's color perception against reference images 900, the colors in the endoscopic video can be adjusted to present an image closer to a standard reference. Team members can have unique individual adjustments effected simultaneously by using dedicated displays, or special eyeglasses equipped with miniature color displays, or a primary display that can switch between color tables on command.

Main Menu settings personalize the default choices for each surgeon. The defaults include the presentation format and color translation tables to display when the Color Map icon is selected 902. Mouse clicking a selection brings it to the primary display window where it is subject to other tools for further analysis as shown in FIG. 9.

Figure 10:
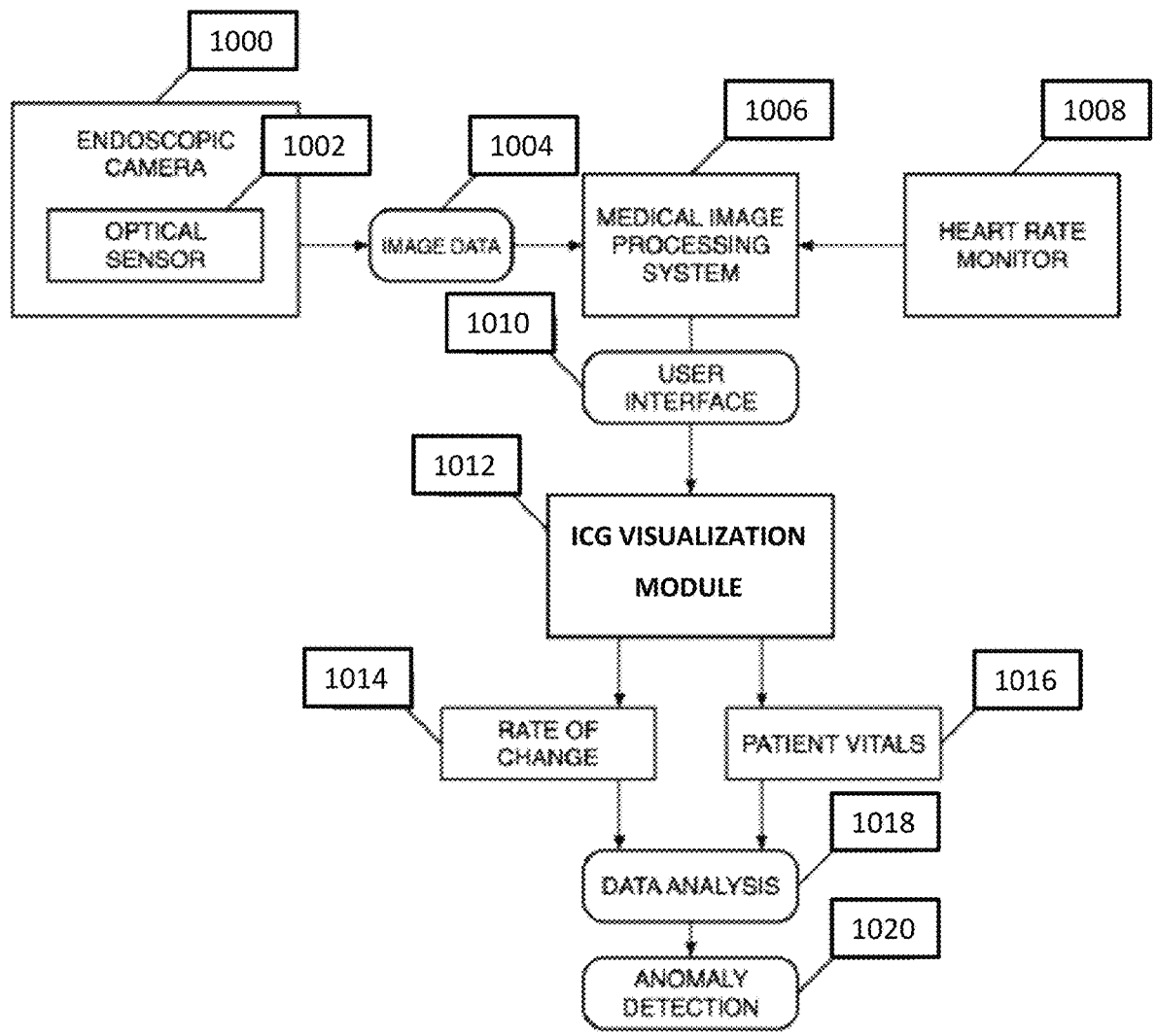
FIG. 10. is a block diagram illustrating the ICG Visualization module within the medical software tools platform.

FIG. 10 is a block diagram illustrating the ICG Visualization module 1012 within the medical software tools platform. In accordance with the preferred embodiment of the present invention, an optical sensor 1002 located within an endoscopic camera lens 1000 registers the color characteristics reflected from a tissue surface. This image data 1004 is transmitted to the medical image processing system 1006, which can also receive data from a device such as a patient heart rate monitor 1008. The medical image processing system 1006 processes and transmits the image data 1004 from the optical sensor with data from the heart rate monitoring device 1008 to the user interface 1010, whereby all sets of data are received through the optical signature measurement module 1012 displaying the rate of change 1014 in the color characteristics simultaneously with the patient vitals data 1016. This data is analyzed 1018 in the module and the results of any anomaly detection 1020 are displayed to the user. The slight changes in one of more of the color components, and the speed at which they change, in relation to a source stimulus (heartbeat, breath, external stimulus) indicates the arrival of blood, contrast agents, or oxygen absorption. Combinations of the components can be used to characterize different types and states of disease and to identify the margins of tumors and diseased areas.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

Embodiments presented are particular ways to realize the invention and are not inclusive of all ways possible. Therefore, there may exist embodiments that do not deviate from the spirit and scope of this disclosure as set forth by appended claims, but do not appear here as specific examples. It will be appreciated that a great plurality of alternative versions are possible.

What is claimed is:

1. A system for medical software tools, comprising:
a first computer input device interface coupled with a first computer system,
a second computer input device interface, configured to plurality of general computer input device interfaces, coupled to said first computer system,
an image stream interface module configured to transmit an image stream from a surgical camera;
a user interface overlay module configured to a first processor in said first computer system to provide a user interface overlay adapted for presentation over said image stream;
an optical sensor corresponding with said surgical camera for registering momentary changes in spectral characteristics reflected from a tissue surface under inspection;
a medical software tools module configured to a surgeon's dashboard on said first computer system, capable of providing a plurality of medical software tools through said user interface module, and wherein said plurality of medical software tools are configured to perform an operation with respect to said image stream and provide an output adapted to be presented over said image stream;
a medical image processing system configured to said first computer system for processing patient medical data and corresponding said patient medical data with said momentary changes in spectral characteristics;
an optical signature, generated by way of said optical sensor, to present data indicative of various patient conditions, and wherein the medical software tool measures: a. changes in color intensity and b. rates at which said color intensities change in response to: heartbeat pushed blood, breathing pushed oxygen or light intensity or modulation from a light source; and
a contrast fluorescent dye, associated with said tissue under inspection to provide an assessment of the perfusion of tissues and organs by identifying areas of highest absorption.

2. The system of claim 1, wherein said medical software tools module features an indocyanine green (ICG) visualization tool.

3. The system of claim 2, wherein said ICG visualization tool utilizes a camera sensor to capture and present color details unforeseen to the human eye.

4. The system of claim 1, further comprising of a color calibration tool for said medical software tools module.

5. The system of claim 1, wherein a display resolution of said image stream can be converted and scaled to add said user interface overlay.

6. The system of claim 1, wherein at least one of said plurality of medical software tools feature a grid tool to mark a location of an anomaly or area of interest during said operation.

7. The system of claim 1, wherein at least one of said plurality of medical software tools include a height mapping module and a perfusion, visualization, quantification and calibration module.

8. A method for medical software tools, comprising:
configuring an image stream interface module to receive an image stream from a surgical camera;
presenting a user interface overlay module to provide a user interface overlay over said image stream;
registering momentary changes in spectral characteristics reflected from a tissue surface under inspection using an optical sensor corresponding with said surgical camera for:
performing an operation with respect to the image stream and provide an output adapted to be presented over said image stream using a medical software tools module configured responsible for providing a plurality of medical software tools through said user interface;
guiding, by way of at least one of said plurality of medical software tools, a medical professional through an operation using said image stream that is presented over said image stream;
processing patient medical data with a medical image processing system,
corresponding said patient medical data with said momentary changes in said spectral characteristics;
generating optical signature data indicative of various patient conditions by way of said optical sensor;
measuring, using at least one of said plurality of medical software tools, changes in color intensity of said tissue surface under inspection and a rate at which said color intensities change in response to: heartbeat pushed blood, breathing pushed oxygen or light intensity or modulation from a light source; and
introducing a contrast fluorescent dye in associated with said tissue under inspection for an assessment of the perfusion of tissues and organs by an analysis of areas of absorption.

9. The method of claim 8, wherein said medical software tools module features an indocyanine green (ICG) visualization tool.

10. The system of claim 9, wherein said ICG visualization tool utilizes a camera sensor to capture and present color details unforeseen to the human eye.

11. The system of claim 8, further comprising of a color calibration tool for said medical software tools module.

12. The system of claim 8, wherein a display resolution of said image stream can be converted and scaled to add said user interface overlay.

13. The system of claim 8, wherein at least one of said plurality of medical software tools feature a grid tool to mark a location of an anomaly or area of interest during said operation.

14. The system of claim 1, wherein at least one of said plurality of medical software tools include a height mapping module and a perfusion, visualization, quantification and calibration module.

15. A system for medical software tools, comprising:
a first computer input device interface coupled with a first computer system;
a second computer input device interface configured to plurality of general computer input device interfaces coupled to said first computer system;
an image stream interface module configured to transmit an image stream from a surgical camera;
a user interface overlay module configured to a first processor in said first computer system to provide a user interface overlay adapted for presentation over said image stream, and wherein said user interface overlay module enables a user to convert, scale and modify the resolution of said image stream presented in said image stream interface module;
wherein said user interface overlay module enables a medical professional to mark an area of interest throughout an operation;
an optical sensor corresponding with said surgical camera for registering momentary changes in spectral characteristics reflected from a tissue surface under inspection;
a medical software tools module configured to a surgeon's dashboard on said first computer system, capable of providing a plurality of medical software tools through said user interface module, and wherein said plurality of medical software tools are configured to perform an operation with respect to said image stream and provide an output adapted to be presented over said image stream;
a medical image processing system configured to said first computer system for processing patient medical data and corresponding said patient medical data with said momentary changes in spectral characteristics;
an optical signature, generated by way of said optical sensor, to present data indicative of various patient conditions, and wherein the medical software tool measures: a. changes in color intensity through a color calibration tool and b. rates at which said color intensities change in response to: heartbeat pushed blood, breathing pushed oxygen or light intensity or modulation from a light source; and
an indocyanine green visualization tool, configured to a camera sensor for visualizing a contrast fluorescent dye in association with said tissue under inspection to provide an assessment of the perfusion of tissues and organs by identifying areas of highest absorption.

16. The system of claim 15, further comprising of said indocyanine green visualization tool using color calibration to determine indocyanine green absorption levels of said area of interest.

17. The system of claim 15, wherein an indocyanine green visualization user interface for said indocyanine green visualization tool is used in conjunction with said user interface overlay module to modify a frame rate and height map of said image stream.

18. The system of claim 15, further comprising of said indocyanine green visualization tool simulating a 3D rendition of an area of high perfusion and absorption of indocyanine green and generate an intensity and speed map of said area of interest.

19. The system of claim 15, wherein an area selected by a mouse can render a compact image of said area of interest while viewing said image stream and simulate a 3D view by mapping said area of interest's pixels on an elevation grid.

20. The system of claim 19, wherein said mouse is used to adjust and modify a view of said compact image by using a plurality of window and level sliders.

* * * * *